US011207255B2

(12) United States Patent
Stebbins et al.

(10) Patent No.: US 11,207,255 B2
(45) Date of Patent: *Dec. 28, 2021

(54) PERFLUORO-FREE SELF-FOAMING FACIAL CLEANSER COMPOSITION

(71) Applicant: L'OREAL, Paris (FR)

(72) Inventors: Nicholas David Stebbins, Clark, NJ (US); Ryuji Hara, Westfield, NJ (US); Susan Halpern Chirch, Basking Ridge, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/526,563

(22) Filed: Jul. 30, 2019

(65) Prior Publication Data

US 2021/0030652 A1 Feb. 4, 2021

(51) Int. Cl.
| | |
|---|---|
| *A61K 8/25* | (2006.01) |
| *A61K 8/44* | (2006.01) |
| *A61K 8/46* | (2006.01) |
| *A61K 8/81* | (2006.01) |
| *A61K 8/89* | (2006.01) |
| *A61K 8/891* | (2006.01) |
| *A61Q 19/00* | (2006.01) |
| *A61Q 19/10* | (2006.01) |
| *C11D 1/00* | (2006.01) |
| *C11D 3/37* | (2006.01) |
| *A61K 8/04* | (2006.01) |

(Continued)

(52) U.S. Cl.
CPC .............. *A61K 8/466* (2013.01); *A61K 8/046* (2013.01); *A61K 8/345* (2013.01); *A61K 8/44* (2013.01); *A61K 8/4926* (2013.01); *A61K 8/8105* (2013.01); *A61K 8/891* (2013.01); *A61Q 19/10* (2013.01)

(58) Field of Classification Search
CPC . A61K 8/046; A61K 8/25; A61K 8/44; A61K 8/46; A61K 8/585; A61K 8/81; A61K 8/89; A61K 8/891; A61Q 19/00; A61Q 19/10; C11D 1/00; C11D 3/162; C11D 3/37; C11D 3/373
See application file for complete search history.

(56) References Cited

U.S. PATENT DOCUMENTS

| | | |
|---|---|---|
| 5,741,509 A | 4/1998 | Kushner |
| 6,172,019 B1 | 1/2001 | Dehan et al. |
| 8,263,114 B2 | 9/2012 | Berlat |
| (Continued) | | |

FOREIGN PATENT DOCUMENTS

| | | |
|---|---|---|
| CA | 2011195 A1 | 8/1990 |
| JP | 2009242340 A | 10/2009 |
| WO | 01/87232 A2 | 11/2001 |

OTHER PUBLICATIONS

Carbopol Polymenr Products, Lubrizol Health, pp. 1-5, https://www.lubrizol.com/Life-Sciences/Products/Carbopol-Polymer-Products, (accessed on Oct. 14, 2019).

*Primary Examiner* — Brian P Mruk

(74) *Attorney, Agent, or Firm* — Laetitia Leproust; Runzhi Zhao

(57) ABSTRACT

A self-foaming cleansing compositions are provided. The self-foaming cleansing composition includes a) of one or more volatile silicone oil; b) one or more surfactants; and c) one or more polymers with suspending properties. The self-foaming cleaning composition is free of perfluoro compound.

14 Claims, 1 Drawing Sheet

(51) Int. Cl.
*A61K 8/34* (2006.01)
*A61K 8/49* (2006.01)

(56) References Cited

U.S. PATENT DOCUMENTS

2002/0122772 A1* 9/2002 Lukenbach ............ A61K 8/042
                                                    424/44
2019/0269604 A1* 9/2019 Kim ..................... A61K 8/44
2021/0030659 A1* 2/2021 Stebbins ............. A61K 8/8147

* cited by examiner

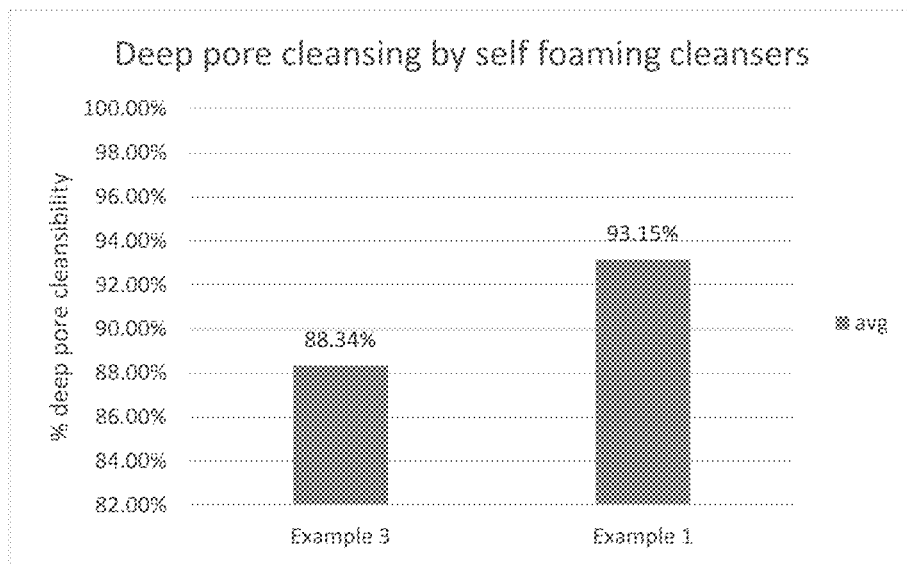

PERFLUORO-FREE SELF-FOAMING FACIAL CLEANSER COMPOSITION

FIELD OF THE DISCLOSURE

The present disclosure relates to self-foaming cleansing compositions that include a combination of volatile silicone oils, a blend of surfactants and polymers with suspending properties in order to obtain self-foaming facial cleansers.

BACKGROUND

Foaming cleansing products have a cleansing action by virtue of the surfactants, which suspend the fatty residues and the pigments of, for example, make-up products. A good foaming property, rinsability, and skin-care property, for example, leaving a good feeling on the skin after rinsing off, such as skin mildness and a moisturizing sensation, are very important for cosmetic foaming cleanser products.

From the consumer's perspective, the amount of the foam directly relates to the perceived cleaning efficiency of the composition. Generally speaking, the larger the volume of foam produced and the more stable the foam, the more efficient is the perceived cleaning action of the composition. Most of these products contain perfluoro compounds. Perfluoro compounds are known to be detrimental for the environments and industries try to not use them.

In view of the remarks above, there is a need to provide a perfluoro free self-foaming cleansing composition for cleaning the skin that foam when in contact with the skin.

SUMMARY OF THE DISCLOSURE

The instant disclosure relates to self-foaming cleansing compositions comprising:
 a) From about 0.5% to about 10% wt. % of one or more volatile silicone oils;
 b) From about 0.5% to about 25% wt. % of one or more surfactants;
 c) From about 0.5% to about 7% wt. % of one or more polymers with suspending properties;
 d) From about 0.5% to about 7% wt. % of one or more hydrophobically-modified polymer thickeners; and
 wherein the weight percentages are based on the total weight of the self-foaming cleansing composition.

The self-foaming cleansing compositions of the instant case are free of perfluoro compound. Despite the lack of the perfluoro compound, the self-foaming cleansing compositions of the instant case can start to self-foam immediately after application of the composition onto the skin. The foam then last at least about 3 minutes or more.

In one or more embodiments, the foaming starts immediately after application of the composition onto the skin.

In some embodiments, the composition is a self-foaming composition.

In one or more embodiments, the self-foaming composition is self-foaming within 10 seconds after application of the cleansing composition onto the skin.

The bubbles or foam may be able to form quickly for example within less than about 10 seconds, within less than about 9 seconds, within less than about 8 seconds, within less than about 7 seconds, within less than about 6 seconds, within less than about 5 seconds, within less than about 4 seconds, within less than about 3 seconds, within less than about 2 seconds, within less than about 1 seconds after application of the cleansing composition onto the skin.

The bubbles or foam according to the instant disclosure may be long-lasting. For example, once the composition is applied to the skin and the foam is formed, the foam may remain substantially intact on the skin for a period of at least about 3 minutes, for a period of at least about 3.5 minutes, for a period of at least about 4 minutes, for a period of at least about 5 minutes, for a period of at least about 8 minutes, for a period of at least about 10 minutes.

In some embodiments, the self-foaming composition is free of perfluoro compounds.

In one or more embodiments, the one or more volatile silicone oils is hexamethyldisiloxane.

In some embodiments, the one or more volatile silicone oils is present in an amount from about 1% to about 8% wt. of the total weight of the self-foaming cleansing composition. In one or more embodiments, the one or more volatile silicone oils is present in an amount from about 1.5% to about 6% wt. of the total weight of the self-foaming cleansing composition.

In some embodiments, the self-foaming cleansing composition is a micro-emulsion.

In some embodiments, the self-foaming cleansing composition is a gel cleanser.

In one or more embodiments, the one or more surfactants is a foaming surfactant.

In some embodiments, the one or more surfactants is selected from coco-betaine, sodium lauroyl sarcosinate, disodium laureth sulfosuccinate (and) sodium lauryl sulfoacetate, sodium lauroyl glutamate, diethylhexyl sodium sulfosuccinate, PEG-7 glyceryl cocoate and a mixture thereof.

In some embodiments, the one or more polymers with suspending properties is present in an amount from about 1% to about 4% wt. of the total weight of the self-foaming cleansing composition. In one embodiment, the one or more polymers with suspending properties is present in an amount from about 1.5% to about 3% wt. of the total weight of the self-foaming cleansing composition.

In some embodiments, the one or more polymers with suspending properties is selected from acrylates copolymer, acrylates crosspolymer, polyacrylate crosspolymer-1, polyacrylate crosspolymer-6, and mixture thereof.

In some embodiments, the one or more volatile silicone oils is volatile after about 10 seconds of application on the skin. In one or more embodiments, the self-foaming cleansing composition starts self-foaming right after application onto the skin.

In some embodiments, the one or more hydrophobically-modified polymer thickeners is selected from acrylates/C10-30 alkyl acrylate crosspolymer, acrylates/C12-alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof.

In some embodiments, self-foaming cleansing compositions may comprise:
 a) From about 0.5% to about 10% wt. % of hexamethyldisiloxane;
 b) From about 2% to about 20% wt. % of one or more surfactants is selected from coco-betaine, sodium lauroyl sarcosinate, disodium laureth sulfosuccinate (and) sodium lauryl sulfoacetate, sodium lauroyl glutamate, diethylhexyl sodium sulfosuccinate, PEG-7 glyceryl cocoate and a mixture thereof;

c) From about 0.5% to about 7% wt. % of one or more polymers with suspending properties is selected from acrylates crosspolymer, polyacrylate crosspolymer-1, polyacrylate crosspolymer-6, and mixture thereof;

d) From about 0.5% to about 7% wt. % of one or more hydrophobically-modified polymer thickeners selected from from acrylates/C10-30 alkyl acrylate crosspolymer, acrylates/C12-22 alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof; and wherein the self-foaming cleansing composition is free of perfluoro compound;

wherein the weight percentages are based on the total weight of the self-foaming cleansing composition.

The self-foaming cleansing compositions are useful for treating the skin, in particular the skin of the face. The compositions can be used as a facial wash, and/or makeup remover, as the products are particularly effective at cleansing the skin.

Some aspects of the instant disclosure can include a method for cleansing the skin comprising applying the composition to the skin and removing at least a portion of the composition from the skin.

The methods generally include applying the self-foaming cleansing compositions to the skin.

The self-foaming cleansing compositions of the instant disclosure provide unexpected foaming once in contact with the skin as well as an unexpected lastingness of the foam thanks to the compositions described in the instant disclosure.

Without being bound by theory or mechanism, it is suggested that the foaming starting at the contact of the skin is due to the combination of a particular volatile oil, a surfactant and one polymer with suspending properties.

It is to be understood that both the foregoing general description and the following detailed description are exemplary and explanatory only, and are not restrictive of the invention.

BRIEF DESCRIPTION OF THE DRAWINGS

FIG. 1 is a graph showing the comparison in % of deep pore cleaning between Example 1 and Example 3.

It should be understood that the various aspects are not limited to the arrangements and instrumentality shown in the figures.

DETAILED DESCRIPTION OF THE DISCLOSURE

The self-foaming cleansing compositions of the instant disclosure, in their broadest sense, typically include the following:

a) From about 0.5% to about 10% wt. % of one or more volatile silicone oils;
b) From about 0.5% to about 25% wt. % of one or more surfactants;
c) From about 0.5% to about 7% wt. % of one or more polymers with suspending properties;
d) From about 0.5% to about 7% wt. % of one or more hydrophobically-modified polymer thickeners; and wherein the weight percentages are based on the total weight of the self-foaming cleansing composition;

wherein the self-foaming cleansing composition is free of perfluoro compound.

As used herein, the term "suspending properties" means that imparts a particular yield value that is sufficient to overcome the effect of gravity or buoyancy of particles or water-insoluble droplets, and is thus able to effectively suspend those particles or droplets.

The cleansing compositions described herein may be free or essentially free of perfluoro compounds.

As used herein, the term "free of perfluoro compound" means that, while it is preferable that no perfluoro is present in the composition of the invention, it is possible to have very small amounts of perfluoro in the compositions, provided that these amounts do not materially affect the advantageous properties of the composition. Most preferably, the compositions contain no perfluoro. To the extent any perfluoro is present in the compositions, it is present at an amount of less than about 2.0% by weight, typically less than about 1.5% by weight, typically less than about 1.0% by weight, typically less than about 0.5% by weight, more typically less than about 0.1% by weight, based on the total weight of the composition. To the extent present, the perfluoro in such compositions are typically contributed by components other than the perfluoro compound.

The self-foaming cleansing compositions disclosed herein foam immediately after application of the composition onto the skin. In some embodiments, the foaming composition is self-foaming within 10 seconds after application of the cleansing composition onto the skin. The foaming, then, last at least about 3 minutes, at least about 3.5 minutes or more.

As used herein, the term "self-bubbling" or "self-foaming" means that it is a composition that exhibits bubbles and/or foam only when applied in a thin layer to the skin without the additional of any other exterior stimuli.

As used herein, the term "foam" means the ability of a composition to produce foam.

As used herein, the term "foam" and "bubble" are used interchangeably throughout the instant disclosure.

Volatile Silicone

The cleansing compositions described herein may contain one or more volatile silicone oils. In some embodiments, the one or more volatile silicone oils, may be, for example an hexamethyldisiloxane. Examples of volatile silicones, may be, for instance volatile linear or cyclic silicone oils, especially those with a viscosity of less than or equal to 8 centistokes (cSt) (8×10−6 m2/s, at 25° C. and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of 5 and 6 cSt, octamethylcyclotetrasiloxane, decamethyl¬cyclo¬penta¬siloxane, cyclohexasiloxane, dodecamethylcyclohexasiloxane, heptamethylhexyltrisiloxane, hepta¬methyl¬octyltrisiloxane, hexamethyldisiloxane, decamethyl¬tetrasiloxane and dodecamethylpentasiloxane, and mixtures thereof.

The total amount of volatile silicone oils may be present in an amount from about 0.5%, 0.6%, 0.7%, 0.8%, 0.95%, 1%, 1.1%, 1.2%, 1.4%, 1.5%, 1.6%, 1.8%, 2%, 2.4%, 2.6%, 2.8%, 3%, 3.2%, 3.4%, 3.6%, 3.8% to about 3.8%, 4%, 4.1%, 4.2%, 4.3%, 4.4%, 4.5%, 4.6%, 4.7%, 4.8%, 4.9%, 5%, 5.2%, 5.4%, 5.6%, 5.8%, 6%, 6.2%, 6.4%, 6.8%, 7%, 7.2%, 7.4%, 7.6%, 7.8%, 8%, 8.2%, 8.4%, 8.6%, 8.8%, 9%, 9.2%, 9.4%, 9.6%, 9.8% or 10% wt. of the total weight of the self-foaming cleansing composition.

Surfactants

In some embodiments, the one or more surfactants may be selected from coco-betaine, sodium lauroyl sarcosinate, disodium laureth sulfosuccinate (and) sodium lauryl sulfoacetate, sodium lauroyl glutamate, diethylhexyl sodium sulfosuccinate, PEG-7 glyceryl cocoate and a mixture thereof.

Surfactants in the composition include a single surfactant or a mixture of surfactants (often surfactant powders or in other easily used forms (liquid)). In one embodiment, the composition includes one or more ionic surfactants that includes anionic or amphoteric surfactants.

Amphotheric Surfactant

Non-limiting amphoteric surfactants include, for example, coco betaine, lauryl betaine, oxyethylenated (10 EO) lauryl betaine, oxyethylenated (10 EO) stearyl betaine, cocamidopropyl betaine, lauramidopropyl betaine and mixtures thereof.

The surfactant in the composition according to the instant disclosure may be one amphoteric surfactant chosen from betaines, (C8-C20)alkyl betaines, (C8-C20)alkylamido(C1-C6)alkylbetaines, and mixtures thereof. Two or more amphoteric surfactants may be used in combination. Thus, a single type of amphoteric surfactant or a combination of different types of amphoteric surfactants may be used.

Examples of amphoteric surfactants include surfactants selected from these classes of surfactants: amphocarboxylates, alkyl betaines, amidoalkyl betaines, amphophosphates, phosphobetaines, pyrophosphobetaines, carboxyalkyl polyamines, and amidoalkyl sultaines. In selected embodiments, the preferred surfactants are those having C10 to C16 in their fatty acyl part.

Mention may in particular be made, as betaines, of (C8-C20)alkyl betaines, such as, for example, coco betaine, such as the product sold under the name Dehyton AB-30® by the company Cognis, lauryl betaine, such as the product sold under the name Genagen KB® by the company Clariant, oxyethylenated (10 EO) lauryl betaine, such as the product sold under the name Lauryl Ether (10 EO) Betaine® by the company Shin Nihon Rica, or oxyethylenated (10 EO) stearyl betaine, such as the product sold under the name Stearyl Ether (10 EO) Betaine® by the company Shin Nihon Rica.

Mention may be made, among (C8-C20)alkylamido(C1-C6)alkylbetaines and derivatives thereof, for example, of cocamidopropyl betaine, sold under the name Lebon 2000 HG® by the company Sanyo or sold under the name Empigen BB® by the company Albright & Wilson, or lauramidopropyl betaine, sold under the name Rewoteric AMB12P® by the company Witco.

Preferably, the amphoteric surfactant is chosen from (C8-C20)alkyl betaines, (C8-C20)alkylamido(C1-C6)alkylbetaines, and mixtures thereof, and preferably among coco betaine, lauryl betaine, oxyethylenated (10 EO) lauryl betaine, oxyethylenated (10 EO) stearyl betaine, cocamidopropyl betaine and mixtures thereof, and more preferably is selected from lauryl betaine, coco betaine and mixtures thereof and still more preferably is coco betaine.

Anionic Surfactants

In some embodiments, one surfactant can be, for example, a compound selected from the group consisting of sodium lauroyl glutamate, sodium lauryl sulfate, disodium lauryl sulfosuccinate, diethylhexyl sodium sulfosuccinate, sodium cocoyl glycinate, potassium cocoyl glycinate, and the mixtures thereof.

In some embodiments, one of the foaming surfactant is disodium lauryl sulfosuccinate.

Examples of anionic surfactants include surfactants selected from these classes of surfactants: alkyl sulfates, alkyl ether sulfates, alkyl monoglyceride sulfates, alkyl monoglyceride sulfonates, alkylaryl sulfates, alkyl sulfosuccinates, alkyl ether sulfosuccinates, alkyl sulfosuccinamates, alkyl ether carboxylates, alkyla idoether carboxylates, alkyl succinates, fatty acyl taurates, fatty acyl isethionates, fatty acyl sarcosinates, fatty acyl glutamates, and alkyl phosphates. Alternative surfactants may include or be combined with foaming surfactants or foaming agents suitable for use in foaming skin cleansers or on skin cleaning fibrous pads when mixed with water. The foaming action provided additional cleaning benefits allowing a crisp clean feel following wash-off by a user.

In selected embodiments, the surfactants are those which can be used in an anhydrous system, such as sodium lauroyl glutamate and diethylhexyl sodium sulfosuccinate.

In alternative embodiments, the surfactant may include suitable nonionic surfactants including alkyl polyglucoside having alkyl groups from C10 to C16.

Other Surfactants

According to the instant disclosure, these surfactants can be chosen from salts, for example, alkali metal salts such as sodium salts, ammonium salts, amine salts, amino alcohol salts and alkaline-earth metal salts.

Examples of alkaline-earth metal salts include magnesium salts of the following types of compounds: acyl isethionates, acyl glycianates, acyl taurates, acyl amino acids, acyl sarcosinates, sulfosuccinates, sulfonates, and sulfoacetates, the alkyl and acyl groups of all these compounds comprising from 6 to 24 carbon atoms (saturated or unsaturated, linear or branched).

Non-limiting examples of acyl amino acids useful in the compositions of the invention include those having the following formula (I):

in which

R is a linear or branched, saturated or unsaturated $C_8$-$C_{16}$ and more preferentially $C_{12}$-$C_{18}$ alkyl chain;

X is an organic cation, for instance an alkanolamine such as triethanolamine, or a mineral cation, for instance an alkali metal such as sodium or potassium, or alternatively ammonia.

Among the preferred radicals R, mention may be made of stearyl, myristyl, oleyl, lauryl and cocoyl.

Among the N-acyl sarcosinates that may be used according to the invention, mention may be made of sodium lauroyl sarcosinate (INCI name: Sodium lauroyl sarcosinate) sold under the name Sarkosyl NL 97® by the company Ciba or sold under the name Oramix L 30® by the company SEPPIC, or sold under the name Amin LS30L by the company Guangzhou Tinci Materials; sodium myristoyl sarcosinate (INCI name: Sodium myristoyl sarcosinate) sold under the name Nikkol Sarcosinate MN® by the company Nikkol, sodium palmitoyl sarcosinate (INCI name: Sodium palmitoyl sarcosinate) sold under the name Nikkol Sarcosinate PN® by the company Nikkol.

Use will be made more particularly of sodium N-lauroyl sarcosinate (INCI name: Sodium lauroyl sarcosinate).

Non-limiting examples of taurates useful in the compositions of the invention include those having the following formula (II):

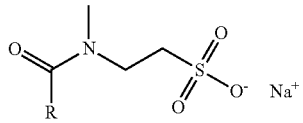
(II)

wherein R is selected from H or an alkyl chain that has 1-24 carbon atoms, said chain being saturated or unsaturated, linear or branched.

A particular taurate that can be used in the current compositions is sodium methyl cocoyl taurate.

Non-limiting examples of isethionates useful in the compositions of the invention include those having the formulas (III) or (IV) below:

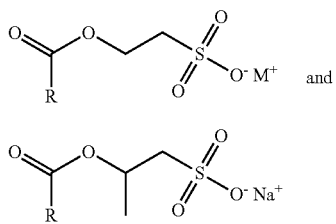
(III)

and (IV)

wherein R is selected from H or an alkyl chain that has 1-24 carbon atoms, said chain being saturated or unsaturated, linear or branched.

Particular isethionates that can be used in the current compositions include, for example, sodium cocoyl isethionate, sodium lauroyl methyl isethionate, and mixtures thereof.

Non-limiting examples of sulfosuccinates useful in the compositions of the invention include those having the following formula (V):

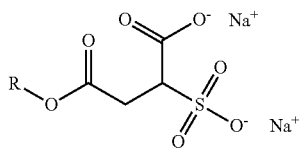
(V)

wherein R is selected from H or an alkyl chain that has 1-24 carbon atoms, said chain being saturated or unsaturated, linear or branched.

A particular sulfosuccinate that can be used in the current compositions is disodium laureth sulfosuccinate.

Non-limiting examples of sulfonates useful in the compositions of the invention include those having the following formula (VI):

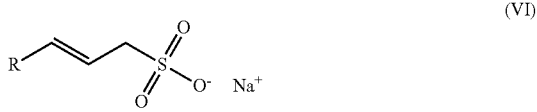
(VI)

wherein R is selected from H or an alkyl chain that has 1-24 carbon atoms, said chain being saturated or unsaturated, linear or branched.

A particular sulfonate that can be used in the current compositions is sodium $C_{14-16}$ olefin sulfonate.

Non-limiting examples of sulfoacetates useful in the compositions of the invention include those having the following formula (VII):

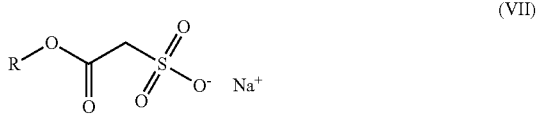
(VII)

wherein R is as defined above for the sulfonates.

A particular sulfoacetate that can be used in the current compositions is sodium lauryl sulfoacetate.

According to one embodiment, the anionic surfactant that is most preferred in the instant disclosure is acyl amino acids useful in the compositions of the invention include those having the following formula (I) as described above, more preferably N-acyl sarcosinates, even more preferably sodium lauroyl sarcosinate (INCI name: Sodium lauroyl sarcosinate).

Non-Sulfate Anionic Surfactants

Useful non-sulfate anionic surfactants include, but are not limited to, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a mixture thereof.

The total amount of one or more surfactants may be present from about 0.5%, 0.6%, 0.7%, 0.8%, 0.9%, 1%, 1.1%, 1.2%, 1.3%, 1.4%, 1.5%, 1.6%, 1.7%, 1.8%, 1.9% 2%, 2.1%, 2.2%, 2.5%, 3%, 3.4%, 3.6%, 3.8%, 4%, 4.2%, 4.4%, 4.6%, 4.8%, 5%, 5.2%, 5.4%, 5.6%, 5.8%, 6%, 6.2%, 6.4%, 6.6%, 6.8%, 7%, 7.2%, 7.4%, 7.6%, 7.8%, 8%, 8.2%, 8.4%, 8.6%, 8.8%, 9%, 9.2%, 9.4%, 9.6%, 9.8%, 10% to about 10%, 10.2%, 10.4%, 10.6%, 10.8%, 11%, 11.2%, 11.4%, 11.6%, 11.8%, 12%, 12.2%, 12.4%, 12.6%, 12.8%, 13%, 13.2%, 13.4%, 13.6%, 13.8%, 14%, 14.2%, 14.4%, 14.6%, 14.8%, 15%, 15.2%, 15.4%, 15.6%, 15.8%, 16%, 16.2%, 16.4%, 16.6%, 16.8%, 17%, 17.2%, 17.4%, 17.6%, 17.8%, 18%, 18.2%, 18.4%, 18.6%, 18.8%, 19%, 19.2%, 19.4%, 19.6%, 19.8%, 20%, 20.2%, 20.4%, 20.6%, 20.8%, 21%, 21.2%, 21.4%, 21.6%, 21.8%, 22%, 22.2%, 22.4%, 22.6%, 22.8%, 23%, 23.2%, 23.4%, 23.6%, 23.8%, 24%, 24.2%, 24.4%, 24.6%, 24.8%, or 25% wt. of the total weight of the self-foaming cleansing.

Rheology Modifiers

Polymer with Suspending Properties

The one or more polymers with suspending properties of the instant disclosure may be chosen from a slightly alkali-swellable cross-linked acrylate polymer contained in an aqueous dispersion comprising about 30% by weight of total solids, a cross-linked anionic acrylate polymer contained in an aqueous dispersion comprising about 32% by weight of total solids, and mixtures thereof.

The slightly alkali-swellable cross-linked acrylate polymer contained in an aqueous dispersion comprising about 30% by weight of total solids is commercially available from the supplier Lubrizol, under the tradename Carbopol® Aqua SF-1 and the INCI name acrylates copolymer.

The cross-linked anionic acrylate polymer contained in an aqueous dispersion comprising about 32% by weight of total solids is commercially available from the supplier Lubrizol, under the tradename Carbopol® Aqua SF-2 and the INCI name acrylates crosspolymer-4.

In some embodiments, the one or more polymers with suspending properties is selected from acrylates crosspolymer, polyacrylate crosspolymer-1, polyacrylate crosspolymer-6, and mixture thereof.

The total amount of one or more polymers with suspending properties of the instant disclosure may be employed in an amount from about 0.5%, 0.6%, 0.7%, 0.8%, 0.9%, 1%, 1.1%, 1.2%, 1.3%, 1.4%, 1.5%, 1.6%, 1.7%, 1.8%, 1.9% 2%, 2.1%, 2.2%, 2.5%, to about 3%, 3.4%, 3.6%, 3.8%, 4%, 4.2%, 4.4%, 4.6%, 4.8%, 5%, 5.2%, 5.4%, 5.6%, 5.8%, 6%, 6.2%, 6.5%, or 7% wt. of the total weight of the self-foaming cleansing composition.

Hydrophobically Modified Poly(meth)acrylates Polymer Thickeners

The hydrophobically-modified acrylic acid based copolymer thickeners useful in the invention compositions are different from "suspending agents" at least in that suspending agents have greater yield stress which enables the stable entrapment of insoluble particle in such suspending agents. In contrast, when used alone, thickeners such as those used herein, typically are not capable of entrapping/suspending insoluble particles such as to create a stable suspension. See, e.g., Technical Data Sheet TDS-244 (Lubrizol Advanced Materials; January, 2002; https://www.lubrizol.com/home-care/documents/technical-data-sheets/tds-244-measurement-understanding-yield-value-personal-care-formulations.pdf).

In some embodiments, the one or more hydrophobically-modified polymer thickeners is selected from acrylates/C10-30 alkyl acrylate crosspolymer, acrylates/C12-alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof.

Non-limiting examples of hydrophobically modified poly (meth)acrylates include acrylates/C10-30 alkyl acrylate crosspolymer, acrylates/C12-22 alkylmethacrylate copolymer, acrylates/steareth-20 methacrylate copolymer, acrylates/steareth (or ceteth)-20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof. In some instances, acrylates/beheneth-25 methacrylate copolymer is particularly preferred. Acrylates/beheneth-25 methacrylate copolymer is commercially available from Lubrizol under the tradename of NOVETHIX-L10 Polymer or from Rohm and Haas (Dow Chemical) under the tradename of ACULYN 28.

In certain exemplary and non-limiting embodiments, the thickening copolymers are chosen from the copolymers resulting from the polymerization of:

at least one monomer of formula (II):

$$CH_2=CH(R1)COOH \qquad (II)$$

wherein $R_1$ is chosen from H or $CH_3$ or $C_2H_5$, providing acrylic acid, methacrylic acid, or ethacrylic acid monomers, and at least one monomer of $(C_{10}-C_{30})$alkyl ester of unsaturated carboxylic acid type corresponding to the monomer of formula (III):

$$CH_2=CH(R2)COOR3 \qquad (III)$$

wherein $R_2$ is chosen from H or $CH_3$ or $C_2H_5$, providing acrylate, methacrylate or ethacrylate units, $R_3$ denoting a $C_{10}-C_{30}$ alkyl radical, such as a $C_{12}-C_{22}$ alkyl radical.

Non-limiting examples of $(C_{10}-C_{30})$alkyl esters of unsaturated carboxylic acids are for example chosen from lauryl acrylate, stearyl acrylate, decyl acrylate, isodecyl acrylate, dodecyl acrylate and the corresponding methacrylates, such as lauryl methacrylate, stearyl methacrylate, decyl methacrylate, isodecyl methacrylate and dodecyl methacrylate, and mixtures thereof.

Additionally, crosslinked thickening polymers may be chosen according to further exemplary embodiments. For example, such polymers may be chosen from polymers resulting from the polymerization of a mixture of monomers comprising:

acrylic acid, an ester of formula (III) described above, in which $R_2$ is chosen from H or $CH_3$, $R_3$ denoting an alkyl radical having from 12 to 22 carbon atoms, and a crosslinking agent, which is a well-known copolymerizable polyethylenic unsaturated monomer, such as diallyl phthalate, allyl (meth)acrylate, divinylbenzene, (poly)ethylene glycol dimethacrylate and methylenebisacrylamide.

By way of example, crosslinked thickening polymers comprising about 60% to about 95% by weight of acrylic acid (hydrophilic unit), about 4% to about 40% by weight of $C_{10}-C_{30}$ alkyl acrylate (hydrophobic unit), and about 0% to about 6% by weight of crosslinking polymerizable monomer. In yet further embodiments, the crosslinked thickening polymers may comprise about 96% to about 98% by weight of acrylic acid (hydrophilic unit), about 1% to about 4% by weight of $C_{10}-C_{30}$ alkyl acrylate (hydrophobic unit), and about 0.1% to 0.6% by weight of crosslinking polymerizable monomer, such as those described above.

Such copolymers may be selected, for example, from acrylate/$C_{10}-C_{30}$ alkyl acrylate copolymers (INCI name: Acrylates/C10-30 Alkyl Acrylate Crosspolymer), such as the products sold by Lubrizol under the trade names PEMULEN™ TR1, PEMULEN™ TR2, CARBOPOL® 1382 and CARBOPOL® EDT 2020.

In further embodiments, the at least one thickening agent may be chosen from nonionic homopolymers or copolymers containing ethylenically unsaturated monomers of the ester and/or amide type. Examples of such agents include the products sold under the names CYANAMER P250 by the company CYTEC (polyacrylamide), methyl methacrylate/ethylene glycol dimethacrylate copolymers (such as PMMA MBX-8C by the company US COSMETICS), butyl methacrylate/methyl methacrylate copolymers (such as ACRYLOID B66 by the company RHOM HMS), and polymethyl methacrylates (BPA 500 by the company KOBO) may be chosen.

We can mention the associative copolymer of the product sold under the commercial name: NOVETHIX L-10 POLYMER® (INCI name: ACRYLATES/BEHENETH-25

METHACRYLATE COPOLYMER) sold by LUBRIZOL, the product sold under the commercial name: Aculyn® 22 (INCI name: ACRYLATES/STEARETH-20 METHACRYLATE COPOLYMER) sold by DOW CHEMICAL, the product sold under the commercial name: Aculyn® 88 (INCI name: ACRYLATES/STEARETH-20 METHACRYLATE CROSSPOLYMER) sold by DOW CHEMICAL, the product sold under the commercial name: STRUCTURE® 2001 (INCI name: ACRYLATES/STEARETH-20 ITACONATE COPOLYMER) sold by AKZO NOBEL, and the product sold under the commercial name: STRUCTURE® 3001 (INCI name: ACRYLATES/CETETH-20 ITACONATE COPOLYMER) sold by AKZO NOBEL.

The one or more hydrophobically-modified polymer thickeners of the instant disclosure may be employed in an amount of from about 0.5%, 0.6%, 0.7%, 0.8%, 0.9%, 1%, 1.1%, 1.2%, 1.3%, 1.4%, 1.5%, 1.6%, 1.7%, 1.8%, 1.9% 2%, 2.1%, 2.2%, 2.5%, to about 3%, 3.4%, 3.6%, 3.8%, 4%, 4.2%, 4.4%, 4.6%, 4.8%, 5%, 5.2%, 5.4%, 5.6%, 5.8%, 6%, 6.2%, 6.5%, or 7% wt. of the total weight of the self-foaming cleansing composition.

Thickening Agents

The self-foaming cleansing compositions may optionally include one or more thickening agents (also referred to as thickeners or viscosity modifying agents). Many thickening agents are water-soluble, and increase the viscosity of water or form an aqueous gel when dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

Gums and Polysaccharides

Non-limiting examples of thickening agents include xanthan gum, guar gum, biosaccharide gum, cellulose, acacia Seneca gum, sclerotium gum, agarose, pechtin, gellan gum, hyaluronic acid.

A wide variety of gums and polysaccharides can be useful herein as gelling agents. "Polysaccharides" refer to gelling agents that contain a backbone of repeating sugar (i.e., carbohydrate) units. Non-limiting examples of polysaccharide gelling agents include those selected from the group consisting of cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename Natrosol® CS Plus from Aqualon Corporation. Further polysaccharides include starch derivatives (for example, starch oxide, dialdehyde starch, dextrin, British gum, acetyl starch, starch phosphate, carboxymethyl starch, hydroxyethyl starch, hydroxypropyl starch).

Other useful polysaccharides include scleroglucans comprising a linear chain of (1-3) linked glucose units with a (1-6) linked glucose every three units, a commercially available example of which is Clearogel™. CS11 from Michel Mercier Products Inc.

Other thickening and gelling agents useful herein include materials which are primarily derived from natural sources. Non-limiting examples of these gelling agents are gums such as acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, and mixtures thereof.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, hydroxypropyl starch).

Optional Components

In some embodiments, the compositions may include optional components selected from the group consisting of actives, fragrance, preservatives, and combinations thereof. The actives are selected from the group consisting of butylated hydroxytoluene, tocopherol, tocopheropl derivatives, tocotrienol, tocotrienol derivatives, ascorbic acid, ascorbic acid derivatives, ascorbyl palmitate, vitamin E, vitamin C, and combinations thereof.

Implementation of the present disclosure is provided by way of the following examples. The examples serve to illustrate the technology without being limiting in nature.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular.

The expression "at least one" means one or more and thus includes individual components as well as mixtures/combinations.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

Example 1

Self-Foaming Cleansing Compositions

The following Examples are provided for illustrative purposes only, and are not intended to be limiting.

TABLE 1

| Inventive and Comparative Examples | | | | | |
|---|---|---|---|---|---|
| Claim Component | Cosmetic type | INCI US | Example 1 | Control Example 2 | Placebo Example 3 |
| a | Silicon | HEXAMETHYLDISILOXANE | 2 | 0 | 0 |
|   | Silicon | DIMETHICONE |   | 2 |   |
| b | Surfactant | COCO-BETAINE | 4.2 | 4.2 | 4.2 |
|   | Surfactant | SODIUM LAUROYL SARCOSINATE | 1.8 | 1.8 | 1.8 |
|   | Surfactant | PEG-7 GLYCERYL COCOATE | 1 | 1 | 1 |
|   | Surfactant | DISODIUM LAURETH SULFOSUCCINATE | 2.16 | 2.16 | 2.16 |
|   |   | (and) SODIUM LAURYL SULFOACETATE | 0.84 | 0.84 | 0.84 |
| c | Polymer | ACRYLATES COPOLYMER | 1.8 | 1.8 | 1.8 |
| d | Hydrophobically-Modified Polymer Thickener; | ACRYLATES/BEHENETH-25 METHACRYLATE COPOLYMER | 0.9 | 0.9 | 0.9 |
|   | Preservatives, pH adjusters, solvents |   | 0.5-5 | 0.5-5 | 0.5-5 |
|   | Solvent | GLYCERIN | 5 | 5 | 5 |
|   | Solvent | WATER | Q.S | Q.S | Q.S |

In making the formulations in the above tables, the following procedure was used.

Generally, the solvents were mixed with the preservatives until dissolved, then the polymer(s) were added until well-dispersed. The pH was adjusted to neutralized the polymer (if necessary). Surfactant(s) were then added and batch was stirred until uniform. Finally, the silicone component was added while simultaneously mixing and homogenizing the batch to properly disperse the silicones. Once homogenous and well-dispersed, the batch was complete.

Example 2

Evaluating the Foaming Cleansers

In this Example, the inventive composition and two Benchmark products were evaluated. The results are shown in Table 2.

TABLE 2

| Inventive Example 1 | Benchmark product 1 | Benchmark product 2 | Time Elapsed |
|---|---|---|---|
| 100% foam remaining | >90% foam remaining | >90% foam remaining | 1 min |
| 100% foam remaining | 70% foam remaining | 70% foam remaining | 2 min |
| 100% foam remaining | 20% foam remaining | 0% foam remaining | 3 min |
| >80% foam remaining | 0% foam remaining | 0% foam remaining | 4 min |

Procedure

In order to collect the data above, the following procedure was used.

An equal amount of the three foaming cleansers was applied to an area on the forearm of a candidate using a single smooth motion without back and forth rubbing. For the remainder of the test, the test areas were not touched. The initial foaming of the three cleansers was assessed visually. At the same time, a timer was started to measure how long the foams will last once applied on the forearm.

The results are presented in Table 2 above.

In the case of the benchmarks products, the foam started to disappeared right after application in the case of both Benchmark, about 20% of foam was remaining in the Benchmark Product 1 after 3 min and was about non-existent in the Benchmark Product 2. The inventive composition performed significantly better than the two Benchmark compositions in its ability to foam instantly and to have the foam lasting for about 3 minutes after application.

Example 3

Cleansing

In this Example, Example 1 and Example 3 were evaluated for their cleansing properties. The results are shown in Table 2.
Study Protocol
For this study, 24 bioskins were employed and divided into 2 groups (6 replicates per group).
Note: Bioskin is a commercially available product made from processed urethane elastomer. It was developed to serve as an artificial skin mimic with similar properties, feel, and resiliency as human skin to be used for in vitro tests.

Group 1: Example 3—placebo cleansing mask
Group 2: Example 1—self-foaming cleansing mask 2. For each group, 1.56 μg/cm2 of sebollution (Sebollution is a lab-made formulation that mimics pollution/particulate matter with grease/oil) was applied on 2.2 cm diameter circle study site on larger pore side of bioskin using finger coat in circular motion and kept for 10 min for drying.
3. They were now washed with pre-treatment cleanser (2 μg/cm2, Water:product=2:1), 10 circles and rinsed under running water (flow rate fixed) for 10 sec and dabbed dry with Kim towels (5 times)
4. Then baseline (TO) readings were taken using a Dermascore instrument. Dermascore is an imaging device that used high powered magnification and carious lighting conditions to observe different facets of skin surface.
5. Now, each group was treated with respective cleansers: product was applied on dry bio skin with 15 circles then kept for 2 mins (to allow it to foam/lather as per procedure) water was applied with 15 circles (2 μg/cm2, Water:product=2:1), rinsed under running water (flow rate fixed) for 30 sec and dabbed dry with Kim towels (5 times)
6. Finally, post treatment readings were taken using Dermascore instrument
7. Finally, all images were analyzed using Dermascore Pilot Software and Number of particles data was used to calculate % removability/deep pore cleansability using below formula—

$$\text{Removability} = \frac{(T_0 - \text{percentage of dark pixels} - T_1 - \text{percentage of dark pixels})}{T_0 - \text{percentage of dark pixels}}$$

The data show that the inventive self-foaming composition, Example 1, significantly deep cleansed the skin compared to Example 3, which did not contain the hexamethyldisiloxane. The data are illustrated in FIG. 1 of the instant disclosure.

While the disclosure has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A self-foaming cleansing composition comprising:
    a) From about 0.5% to about 10% wt. % of one or more volatile silicone oil;
    b) From about 0.5% to about 25% wt. % of one or more surfactants;
    c) From about 0.5% to about 7% wt. % of one or more polymers with suspending properties is selected from a slightly alkali-swellable cross-linked acrylate polymer contained in an aqueous dispersion;
    d) From about 0.5% to about 7% wt. % of one or more hydrophobically-modified polymer thickener; and
    wherein the self-foaming cleansing composition is free of perfluoro compound;
    wherein the weight percentages are based on the total weight of the self-foaming cleansing composition.

2. The self-foaming cleansing composition of claim 1, wherein the foaming starts immediately after application of the composition onto the skin.

3. The self-foaming cleansing composition of claim 1, wherein the foaming last at least about 3 minutes.

4. The self-foaming cleansing composition of claim 1, wherein the one or more volatile silicone oils is hexamethyldisiloxane.

5. The self-foaming cleansing composition of claim 4, wherein the one or more volatile silicone oils is present in an amount from about 1% to about 8% wt. of the total weight of the self-foaming cleansing composition.

6. The self-foaming cleansing composition of claim 5, wherein the one or more volatile silicone oils is present in an amount from about 1.5% to about 6% wt. of the total weight of the self-foaming cleansing composition.

7. The self-foaming cleaning composition of claim 1, wherein the one or more surfactants is a foaming surfactant.

8. The self-foaming cleaning composition of claim 1, wherein the one or more surfactants is selected from coco-betaine, sodium lauroyl sarcosinate, disodium laureth sulfosuccinate, sodium lauryl sulfoacetate, sodium lauroyl glutamate, diethylhexyl sodium sulfosuccinate, PEG-7 glyceryl cocoate and a mixture thereof.

9. The self-foaming cleansing composition of claim 1, wherein the one or more polymers with suspending properties is present in an amount from about 1% to about 4% wt. of the total weight of the self-foaming cleansing composition.

10. The self-foaming cleansing composition of claim 9, wherein the one or more polymers with suspending properties is present in an amount from about 1.5% to about 3% wt. of the total weight of the self-foaming cleansing composition.

11. The self-foaming cleansing composition of claim 1, wherein the one or more hydrophobically-modified polymer thickeners is selected from acrylates/C10-30 alkyl acrylate crosspolymer, acrylates/C12-22 alkylmethacrylate copolymer, acrylates/steareth-20 methacrylate copolymer, acrylates/steareth 20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof.

12. A self-foaming cleansing composition comprising:
    a) From about 0.5% to about 10% wt. % of hexamethyldisiloxane,
    b) From about 2% to about 20% wt. % of one or more surfactants is selected from coco-betaine, sodium lauroyl sarcosinate, disodium laureth sulfosuccinate, sodium lauryl sulfoacetate, sodium lauroyl glutamate, diethylhexyl sodium sulfosuccinate, PEG-7 glyceryl cocoate and a mixture thereof,
    c) From about 0.5% to about 7% wt. % of one or more polymers with suspending properties is selected from acrylates crosspolymer, polyacrylate crosspolymer-1, polyacrylate crosspolymer-6, and mixture thereof,
    d) From about 0.5% to about 7% wt. % of one or more hydrophobically-modified polymer thickener selected from acrylates/C10-30 alkyl acrylate crosspolymer, acrylates/C12-22 alkylmethacrylate copolymer, acrylates/steareth-20 methacrylate copolymer, acrylates/steareth 20 itaconate copolymer, acrylates/steareth-50 acrylate copolymer, steareth-10 allyl ether/acrylate copolymer, acrylates/beheneth-25 methacrylate copolymer, acrylates/vinyl acetate crosspolymer, glyceryl polymethacrylate, ammonium acryloyldimethyltaurate/beheneth-25 methacrylate copolymer, and a mixture thereof, wherein the self-foaming cleansing composition is free of perfluoro compound;

wherein the weight percentages are based on the total weight of the self-foaming cleansing composition.

13. A method for cleansing the skin comprising applying the composition of claim 1 to the skin and removing at least a portion of the composition from the skin.

14. A method for cleansing the face comprising applying the cleansing composition of claim 1 to the face and cleansing the face.

\* \* \* \* \*